United States Patent [19] [11] 3,988,247
Dieckelmann et al. [45] Oct. 26, 1976

[54] SULFONATED LUBRICATING AGENTS FOR LEATHER AND FURS AND PROCESS

[75] Inventors: Gerhard Dieckelmann; Jurgen Plapper, both of Hilden; Horst Baumann, Leichlingen; Werner Stein, Erkrath-Unterbach, all of Germany

[73] Assignee: Henkel & Cie G.m.b.H., Dusseldorf, Germany

[22] Filed: Aug. 24, 1973

[21] Appl. No.: 391,201

[30] Foreign Application Priority Data

Sept. 14, 1972  Germany.......................... 2245077

[52] U.S. Cl. ................................ 252/8.7; 8/94.22; 8/94.23; 260/399; 260/400; 260/408
[51] Int. Cl.² .................................................. C14C 9/02
[58] Field of Search ........................ 8/94.22, 94.33; 252/8.57; 260/408

[56] References Cited
UNITED STATES PATENTS

| | | | |
|---|---|---|---|
| 408,360 | 7/1889 | Sommer | 8/94.22 X |
| 1,117,912 | 11/1914 | Rohm | 8/94.22 X |
| 1,957,324 | 5/1934 | Dambacher | 252/8.57 |
| 2,115,509 | 4/1938 | Jaeger | 8/94.22 X |
| 2,118,308 | 5/1938 | Jaeger | 252/8.57 |
| 2,974,000 | 3/1961 | Retzsch et al. | 8/94.23 |
| 3,370,005 | 2/1968 | Stein et al. | 252/8.57 |
| 3,724,999 | 4/1973 | Stein et al. | 252/8.57 |

FOREIGN PATENTS OR APPLICATIONS 2,031,167  11/1970  France .............................. 252/8.57

*Primary Examiner*—Howard E. Schain
*Attorney, Agent, or Firm*—Hammond & Littel

[57] ABSTRACT

Process and agent for fatting or lubrication of leather and furs based on the salts of sulfonated chlorinated products of higher fatty acids or of esters of higher fatty acids, said fatty acids having from 8 to 24 carbon atoms, especially natural fats and oils or tallow fatty acid methyl ester, having a chlorine content of 20% to 45% by weight and essentially free of olefinic double bonds and having an $SO_3$ content of from 40 to 150 mol percent based on the chlorinated product, which agent and the leather and furs so treated are extraordinarily resistant to the effect of light, to oxidation and to acids.

6 Claims, No Drawings

SULFONATED LUBRICATING AGENTS FOR LEATHER AND FURS AND PROCESS

THE PRIOR ART

In general, water-emulsifiable leather and fur fatting agents and lubricants are produced by sulfating unsaturated natural or synthetic fats, oils or waxes with the usual sulfating agents such as commercial sulfuric acid or oleum. As a rule, sulfation is continued only until sufficient emulsifiability is attained, the sulfation products obtained still have a considerable iodine number. However, the unsaturated character of these products influences unfavorably their oxidation stability and, hence, the shelf life of the lubricants as well as the light resistance of the leather and furs lubricated with them. Furthermore, the sulfuric acid esters formed by sulfation have little resistance to acid action in the leather and readily become saponified, thereby making it possible for free fatty acids to form and, if saturated fatty acids are present in sufficient quantity, fatty acid exudation to develop.

This drawback is eliminated, according to U.S. Pat. No. 3,370,005, by reducing the number of double bonds by 20 to 70% by partial chlorination of the unsaturated raw materials. The subsequent sulfation yields lubricants with improved properties regarding light resistance and shelf life, but even these products are sensitive to acid and not entirely stable in storage.

Finally, leather lubricants are known from both U.S. Pat. No. 3,300,525 and French Pat. No. 2,031,167 which are obtained from sulfonation and, possibly partial chlorination of unsaturated natural or synthetic fatty acid esters. $SO_3$, mixed with inert gases, if applicable, is used as the sulfonating agent. Due to their content of genuine sulfonates, such sulfonation products are acid-resistant. But they retain a partially unsaturated character so that a degree of oxidation sensitivity and light sensitivity remains. Also the sulfonation of unsaturated substances with sulfur trioxide is diffucult because of the occurring strong oxidation reaction which makes it hard to prevent dark discolorations and undesired polymerizations. Not even a subsequent treatment of such sulfonates by means of the usual bleaching agents can eliminate the above disadvantages.

OBJECTS OF THE INVENTION

An object of the invention is lubricants for leather and furs which avoid the above-mentioned disadvantages. They are characterized by their content of sulfonated chlorination products of higher fatty acids or esters of higher fatty acids having from 8 to 24 carbon atoms with a chlorine content from 20 to 45% by weight and containing essentially no olefinic double bonds, in the form of their alkali, ammonia or amino salts.

Another object of the invention is the development of a sulfonated lubricating agent for leather and tanned furs consisting of a salt of a sulfonated, chlorinated higher fatty acid compound selected from the group consisting of higher fatty acids having from 8 to 24 carbon atoms, esters of said higher fatty acids with alcohols selected from the group consisting of alkanols having 1 to 24 carbon atoms, alkanediols having 2 to 6 carbon atoms, alkanetriols having 3 to 6 carbon atoms, alkanetetraols having from 4 to 6 carbon atoms and alkanehexaols having 6 carbon atoms, and naturally occurring fats, oils and waxes containing fatty acids having 8 to 24 carbon atoms, said sulfonated chlorinated higher fatty acid compound having a chlorine content of 20 to 45% and essentially free of olefinic double bonds and having an $SO_3$ content of from 40 to 150 mol percent based on the chlorinated product and being in the form of a salt selected from the group consisting of alkali metal salts, ammonium salts and lower alkylol ammonium salts.

A further object of the present invention is the development of a process for the production of a sulfonated lubricating agent for leather and tanned furs consisting of the steps of chlorinating a fatty acid compound selected from the group consisting of higher fatty acids having from 8 to 24 carbon atoms, esters of said higher fatty acids with alcohols selected from the group consisting of alkanols having 1 to 24 carbon atoms, alkanediols having 2 to 6 carbon atoms, alkanetriols having 3 to 6 carbon atoms, alkanetetraols having from 4 to 6 carbon atoms and alkanehexaols having 6 carbon atoms, and naturally occurring fats, oils and waxes containing fatty acids having 8 to 24 carbon atoms, with chlorine at a temperature of 20° to 100°C for a time sufficient to attain a chlorine content of from 20 to 45% by weight and where said chlorinated fatty acid compound is substantially free of olefinic double bonds, sulfonating said chlorinated fatty acid compound with $SO_3$ at a temperature of 0° to 90°C for a time sufficient to attain an $SO_3$ content of from 40 to 150 mol percent based on the chlorinated fatty acid compound, and recovering said sulfonated lubricating agent.

A yet further object of the invention is the improvement in the process of treating leather and tanned furs by contacting them with an aqueous solution of an emulsifiable lubricating agent which comprises using said sulfonating lubricating agent described above.

These and other objects of the present invention will become more apparent as the description thereof proceeds.

DESCRIPTION OF THE INVENTION

The drawbacks of the prior art have been overcome and the above objects achieved by the development of a sulfonated lubricating agent for leather and tanned furs consisting of a salt of a sulfonated, chlorinated higher fatty acid compound selected from the group consisting of higher fatty acids having from 8 to 24 carbon atoms, esters of said higher fatty acids with alcohols selected from the group consisting of alkanols having 1 to 24 carbon atoms, alkanediols having 2 to 6 carbon atoms, alkanetriols having 3 to 6 carbon atoms, alkanetetraols having from 4 to 6 carbon atoms and alkanehexaols having 6 carbon atoms, and naturally occurring fats, oils and waxes containing fatty acids having 8 to 24 carbon atoms, said sulfonated chlorinated higher fatty acid compound having a chlorine content of 20 to 45% and essentially free of olefinic double bonds and having an $SO_3$ content of from 40 to 150 mol percent based on the chlorinated product and being in the form of a salt selected from the group consisting of alkali metal salts, ammonium salts and lower alkylol ammonium salts.

Due to the lack of double bonds, the light and oxidation resistance of the lubricants of the invention is extraordinarily good. Their adhesion to the leather fiber is excellent so that there is no migration, staining or exudation. The claimed lubricants are also quite resistant to the action of solvents. The leathers or tanned furs treated according to the invention are further characterized by their particularly pleasant, soft and lardy feel as well as the beautiful sheen of their fur hair.

To produce the lubricants of the invention, it is preferred to start with naturally occurring higher fatty acids or esters of higher fatty acids having from 8 to 24, preferably 10 to 20, carbon atoms. Mixtures of fatty acids or fats or oils as present in naturally occurring aliphatic substances, especially those with a share of singly or repeatedly unsaturated fatty acids are preferred. Preferably the starting material is a fatty acid compound selected from the group consisting of higher fatty acids having from 8 to 24 carbon atoms, esters of said higher fatty acids with alcohols selected from the group consisting of alkanols having 1 to 24 carbon atoms, alkanediols having 2 to 6 carbon atoms, alkanetriols having 3 to 6 carbon atoms, alkanetetraols having from 4 to 6 carbon atoms and alkanehexaols having 6 carbon atoms, and naturally occurring fats, oils and waxes containing fatty acids having 8 to 24 carbon atoms. Examples of such fatty acid compounds are coconut oil, soybean oil, cottonseed oil, rapeseed oil, linseed oil, castor oil, sunflowerseed oil, olive oil, neat's foot oil, peanut oil, herring oil, cod liver oil, shark liver oil, whale oil, tallow fat or lard, furthermore the fatty acid mixture obtained from these fats or oils, and the naturally occurring wax esters such as sperm oil. But even aliphatic fatty acid compounds containing no unsaturated fatty acids or with a reduced content of unsaturated fatty acids such as the saturated fats obtained by pressing, crystallization or distillation, or partially or completely hardened fats or oils can be utilized as starting materials.

Also suited as raw materials for the manufacture of the lubricants are synthetically produced esters of saturated or unsaturated fatty acids having from 8 to 24, preferably 10 to 20, carbon atoms, such as decanecarboxylic acid, palmitic acid, stearic acid, behenic acid, dodecenecarboxylic acid, oleic acid, linoleic acid or alkanoic acids produced by paraffin oxidation, with mono- or poly-hydric aliphatic alcohols having from 1 to 6 carbon atoms, such as methanol, ethanol, isopropanol, butanol, ethyleneglycol, 1,2-propyleneglycol, glycerin, pentaerythrite or sorbitol, or higher alcohols having 8 to 24 carbon atoms, such as decylalcohol or oleylalcohol.

Due to their ready availability the natural animal or vegetable fats, oils or waxes and the products obtained from ester interchange with lower alkanols, in particular, methyl alcohol, and the corresponding fatty acid mixtures are preferred as raw materials.

The process of the invention is preferably for the production of a sulfonated lubricating agent for leather and tanned furs consisting of the steps of chlorinating a fatty acid compound selected from the group consisting of higher fatty acids having from 8 to 24 carbon atoms, esters of said higher fatty acids with alcohols selected from the group consisting of alkanols having 1 to 24 carbon atoms, alkanediols having 2 to 6 carbon atoms, alkanetriols having 3 to 6 carbon atoms, alkanetetraols having from 4 to 6 carbon atoms and alkanehexaols having 6 carbon atoms, and naturally occurring fats, oils and waxes containing fatty acids having 8 to 24 carbon atoms, with chlorine at a temperature of 20° to 100° C for a time sufficient to attain a chlorine content of from 20 to 45% by weight and where said chlorinated fatty acid compound is substantially free of olefinic double bonds, sulfonating said chlorinated fatty acid compound with $SO_3$ at a temperature of 0° to 90° C for a time sufficient to attain an $SO_3$ content of from 40 to 150 mol percent based on the chlorinated fatty acid compound, and recovering said sulfonated lubricating agent.

The raw materials mentioned are first subjected to a chlorination treatment carried out in known manner. The commonly used methods of chlorine addition are made use of, such as the introduction of gaseous chlorine into the raw material to be chlorinated, it being possible to dilute the mixture, if desired, with an organic solvent such as carbon tetrachloride. The chlorine may be diluted with inert gases such as nitrogen. In general, the procedure is to chlorinate at room or slightly elevated temperature first, until the possibly present double bonds are saturated. Then, chlorine introduction is continued at temperatures between about 40° to 100° C until the desired degree of chlorination is reached by substitution of hydrogen atoms by chlorine. It is recommended to conduct the process in the presence of the light of a mercury vapor lamp or of another UV light source, at least at the start of the substitution chlorination. It is advantageous to continue the irradiation to the conclusion of the chlorination. In any event, provisions should be made by appropriate cooling to dissipate the developing reaction heat in order to avoid damage through side reactions.

The purpose of the chlorination is essentially to saturate all the double bonds present in the fatty acid compound starting material and to obtain, in the end product, a chlorine content of 20 to 45%, by weight.

Solid raw materials change into liquid-to-pasty state due to the chlorination so that chlorination products of relatively low melting points are obtained, which is of advantage for the subsequent sulfonation. After chlorination it is expedient to eliminate the dissolved HCl by-product possibly present in the substance. For this purpose it is possible to blow the reaction mixture at as low a temperature as possible with dry air, nitrogen, carbon dioxide or another inert gas until the hydrogen chloride content is sufficiently low.

Sulfonation is carried out with $SO_3$ in known manner. It is common practice to use $SO_3$-air mixtures with a content of 2 to 20% by volume, preferably 4 to 8%, by volume of $SO_3$, but other inert gases such as nitrogen, carbon dioxide or the like may also be used as dilutants.

Sulfonation is carried out at temperatures between 0° and 90° C. In order to obtain sulfonation products with as light in color as possible it is expedient to work within this temperature range at temperature as low as possible. It may also be expedient to subject the chlorination products to sulfonation in an indifferent orga solvent. The reaction between the chlorination products and the $SO_3$ takes place with formation of nonhydrolyzable sulfonate groups. Striven for is an $SO_3$-absorption of between 40 to 150, preferably 40 to 100, mol percent, relative to the chlorination products.

Neutralization is accomplished with alkali metal hydroxides such as NaOH or KOH in aqueous solution or, preferably, with an ammonia solution or with an aliphatic or cycloaliphatic amine, such as alkylamines, dialkylamines, trialkylamines and cyclohexylamines having 1 to 6 carbon atoms, or an alkanolamine having 2 to 6 carbon atoms, such as triethanolamine. Liquid, highly concentrated, water-emulsifiable products of excellent oxidation, light and acid resistant, are obtained which are signally suited for the lubrication of light-colored, pastel-tinted and white leathers as well as for the lubrication of even valuable and sensitive tanned furs.

If dark-colored or more unsaturated raw materials are used, bleaching the sulfonation products may be recommended. This is accomplished in the usual manner by adding small quantities of approximately 0.5 to 5%, preferably 1 to 4%, $H_2O_2$ solutions to the acid sulfonation product at temperatures between 20° and 80° C, preferably between 40° and 60° C. Through this measure it is possible to lighten dark-colored sulfonation products very considerably.

The products are used in the usual manner in the form of aqueous emulsions for the fat-liquoring or leather or for the treatment of furs. Preferably the sulfonated lubricants of the invention are applied to the leather and tanned furs by treating the leather in vats at a temperature of from 40° to 80° C, preferably 60° C, with a float or aqueous liquor of 80 to 250%, preferably 100 to 120%, containing from 3 to 10% of the sulfonated lubricants of the invention, both based on the amount of the leather or tanned furs being treated.

The products of the invention are self-emulsifying so that the supplemental addition of emulsifiers is generally not required. However, to achieve specific effects, the sulfonation products may be combined with the corresponding unsulfonated chlorination products or other conventional leather treatment agents, such as unsulfonated oils or fats, for example, fish oil, sperm oil, neat's-foot oil and the like, or synthetic lubricants such as chloroparaffin, paraffin sulfonates, sulfated native fats or oils or synthetic fatty acid esters, or mineral oils or the like, possibly in connection with anionic, non-ionogenic or cationic emulsifers, preferably non-ionic surface-active compounds, such as ethyleneoxide addition products to higher fatty alcohols, alkylphenols or alkylamines having 10 to 20 carbon atoms in the alkyl. Stabilization of the products may be accomplished by rendering hydrogen chloride residues possibly still present or newly formed harmless by means of epoxy compounds in amounts from 0.5 to 5% by weight. Pertinent examples are: glycide, epichlorohydrin, glycidyl ethers of mono- or polyhydric alcohols, such as glycol, glycerin or sorbitol as well as epoxidized fats such as epoxidized soy bean oil, linseed oil or oleic acid butylester.

The products are well absorbed by the leather and yield excellent lubricating and softening action, with a remarkable resistance to water and aqueous or organic detergent solutions. Their tendency to migrate under thermal stress is minimal so that fusing operations or the vulcanization of rubber soles to shoe uppers can be carried out without difficulties. The good light, oxidation and acid resistance of the sulfonated products of the invention, which also makes them suitable for the lubrication of sensitive and light-colored leathers and furs, is to be particularly emphasized.

The following specific embodiments are illustrative of the practice of the invention without being limitative in any respect.

EXAMPLE 1

Tallow fatty acid methyl ester (Iodine No. 53) was chlorinated to a content of 30% by weight by the introduction of chlorine with simultaneous radiation by a UV lamp. The chlorinated tallow fatty acid methyl ester obtained was essentially free of double bonds.

The subsequent sulfonation was carried out in a cylindrical glass vessel with cooling jacket. 440 gm (1.08 mol) of the chlorinated tallow fatty acid methyl ester were charged into the vessel, and an $SO_3$-air mixture containing approximately 3% of $SO_3$ by volume was introduced into the ester through a gas inlet tube at the rate of approximately 800 liters per hour. 65 gm of $SO_3$ (0.81 mol) were caused to react in the course of 50 minutes. By circulating water heated to 70° to 75° C, the reaction temperature was kept at 80° to 85° C. The reaction was allowed to continue for another 10 minutes after the conclusion of the $SO_3$ introduction, with air passing through the vessel.

Then 470 gm of the sulfonation product were mixed in batches in a beaker with a total of 48 gm of a 30% $H_2O_2$ solution while stirring and maintaining a temperature from 50° to 60° C. The originally dark sulfonation product assumed a honey yellow color in the course of the bleaching operation. The bleached product was neutralized by adding 71 gm of a 25% $NH_3$ solution. 587 gm of a yellowish, pasty product were obtained.

Shoe uppers retanned with synthetic tanning agents or shoe uppers retanned with resinous tanning agents were fat-liquored in the vat at 60° C for 45 minutes with 100 to 120% liquor and 5 to 6% of the chlorinated sulfonation product obtained above as the lubricating substance, based on the leather. The leather, dried and finished in the usual manner, was characterized by its soft, supple and full feel, good pitting resistance and excellent resistance to light and oxidation.

EXAMPLE 2

As described in EXAMPLE 1, 415 gm of a chlorinated tallow fatty acid methyl ester (1.02 mol) containing 3% by weight chlorine were caused to react with 37 gm of $SO_3$ (0.45 mol) by introducing an $SO_3$-air mixture containing about 3% $SO_3$ by volume in the course of 30 minutes at 80° to 85° C. After the conclusion of the after-reaction at 80° to 85° C, 434 gm of the sulfonation product were bleached at 50° to 60° C with a total of 45 mg of a 30% $H_2O_2$ solution. After the neutralization of the bleached, yellowish sulfonation product with 44 gm of a 25% $NH_3$ solution, 516 gm of a yellowish pasty product containing 84% active substance were obtained.

Chromium-tanned and dyed apparel leather was fat-liquored in the vat at 60° C for 45 minutes with 100% liquor and 6 to 8% lubricating substance consisting of a mixture of 80% by weight of the above-described chlorinated sulfonation product and 20% by weight of the corresponding unsulfonated, chlorinated tallow fatty acid methyl ester, both based on the leather.

The leather, dried and finished in the usual manner, was characterized by its soft, supple and full feel and by its excellent light and oxidation resistance.

EXAMPLE 3

As described in Example 1, a chlorinated tallow fatty acid methyl ester containing 41% by weight chlorine was subjected to sulfonation. 350 gm of the chlorinated tallow fatty acid methyl ester (0.73 mol) were caused to react in the process with 35 gm of $SO_3$ (0.44 mol) in the course of 30 minutes at 80° to 85° C by introducing an $SO_3$-air mixture containing 3% by volume of $SO_3$. The after-reaction was carried out at 80° to 85° C. Bleaching of 362 gm of the sulfonation product at 50° to 60° C with a total of 37 gm of a 30 % $H_2O_2$ solution followed. After the neutralization of the bleached, yellowish sulfonation product with 40 gm of a 25% NH₃ solution, 436 gm of a yellowish, pasty product containing 81% active substance were obtained.

Pastel-tinted, chromium-tanned lambskin glove leather was fat-liquored in the vat at 60° C for 45 minutes with 100% liquor and 4 to 6% lubricant consisting of a mixture of 75% of the above-described chlorinated sulfonation product, 21% of the corresponding unsulfonated, chlorinated tallow fatty acid methyl ester and 4% of tallow amine adducted with 4 mols of ethyleneoxide, based on the leather, after which the leather was dried and finished in the usual manner.

The leather was characterized by its pliant, supple feed and good light resistance.

EXAMPLE 4

350 gm (0.73 mol) of the chlorinated tallow fatty acid methyl ester of Example 3 were caused to react with 23 gm of SO₃ (0.29 mol) by introducing an SO₃-air mixture containing about 3% by volume SO₃, at the rate of 600 liters/hour in the course of about 20 minutes at 80° to 85° C. Bleaching of 358 gm of this sulfonation product at 50° to 60° C with a total of 37 gm of a 30% H₂O₂ solution followed the after-reaction. The neutralization of the bleached sulfonation product with 26.5 gm of a 25% NH₃ solution yielded 417 gm of a bleached, yellow, pasty product containing 85% active substance.

Chromium-tanned and dyed cowhide apparel leather was fat liquored in the vat at 60° C for 45 minutes with 100% liquor and 6 to 8% of a lubricant consisting of a mixture of 76% of the above-described chlorinated sulfonation product, 20% of the corresponding unsulfonated chlorinated ester and 4% of a mixture of commercial aliphatic alcohols of the chain lengths $C_{12}$ to $C_{18}$ adducted with 8 mols of ethyleneoxide, based on the leather.

The leather, dried and finished in the usual manner, was characterized by its soft, supple and full feel and by its excellent light and oxidation resistance.

EXAMPLE 5

233 gm (0.33 mol) of a chlorinated caprylic-caprinic-(7:3)-acid triglyceride, containing 29% by weight chlorine, was reacted with 26.7 gm of SO₃ (0.33 mol) in the course of 30 minutes at 80° C to 85° C by introducing an SO₃-nitrogen mixture containing 2% by volume of SO₃. The after-reaction was carried out at 80° C to 85° C. The neutralization of the sulfonation product with 80 gm of a 25% NH₃ solution yielded 324 gm of a yellow, pasty product containing 85% active substance.

The product was used for fat liquoring of chromium-tanned leather as in Example 4.

EXAMPLE 6

396 gm (0.33 mol) of a chlorinated oleic acid-triglyceride containing 25% by weight chlorine, was reacted with 33.5 g of SO₃ (0.42 mol) in the manner of Example 5. After bleaching and neutralization with 40 gm of a 25% NH₃ solution, 450 g of a yellow-brown, pasty product containing 94% active substance was obtained.

The product was used like the one of Example 4.

EXAMPLE 7

401 gm (0.5 mol) of a chlorinated sperm oil, containing 23% by weight chlorine, were reacted with 30 gm of SO₃ (0.375 mol) in the manner of Example 5. The neutralization of the sulfonation product with 40 gm of a 24% NH₃ solution yielded 465 gm of a yellowish, pasty product containing 94% active substance.

The product was used like the one of Example 4.

The preceding specific embodiments are illustrative of the practice of the invention. It is to be understood, however, that other expedients known to those skilled in the art or disclosed herein may be employed without departing from the spirit of the invention or the scope of the appended claims.

We claim:
1. A process for the production of a sulfonated lubricating agent for leather and tanned furs consisting of the steps of: chlorinating an at least partially unsaturated fatty acid compound selected from the group consisting of esters of naturally occurring mixtures of higher fatty acids having from 8 to 24 carbon atoms with alcohols selected from the group consisting of alkanols having 1 to 24 carbon atoms, alkanediols having 2 to 6 carbon atoms, alkanetriols having 3 to 6 carbon atoms, alkanetetraols having from 4 to 6 carbon atoms and alkanehexaols having 6 carbon atoms, and naturally occurring unsaturated fats, oils and waxes containing fatty acids having 8 to 24 carbon atoms, with chlorine at a temperature of about room temperature until the double bonds in said fatty acid compounds are chlorinated and thereafter at a temperature of 40° to 100° C. under UV irradiation for a time sufficient to attain chlorine content of from 20 to 45% by weight, sulfonating said chlorinated fatty acid compound with SO₃ at a temperature of 80° to 85°C. for a time sufficient to attain an SO₃ content of from 40 to 150 mol percent based on the chlorinated fatty acid compound, and forming a water-emulsifiable alkali metal, ammonium, or lower alkyl-ammonium salt of said compound.

2. The process of claim 1 wherein said SO₃ content is from 40 to 100 mol percent, based on the chlorinated fatty acid compound.

3. The process of claim 1 wherein said fatty acid compound is a naturally occurring fat or oil.

4. The process of claim 1 wherein said fatty acid compound is an ester of a naturally occurring fatty acid with an alkanol having 1 to 6 carbon atoms.

5. The process of claim 1 wherein said fatty acid compound is a tallow fatty acid methyl ester.

6. A sulfonated lubricating agent for leather and tanned furs prepared by the process of claim 1.

* * * * *